United States Patent

O'Farrell, Jr. et al.

[11] Patent Number: 5,802,719
[45] Date of Patent: Sep. 8, 1998

[54] ONE PIECE C-ARM FOR X-RAY DIAGNOSTIC EQUIPMENT

[75] Inventors: Frank B. O'Farrell, Jr.; Alfred P. Tomasino, both of Sandy; Roy J. Orr, Salt Lake City; Robert G. Buckingham, Salt Lake City; Barry K. Hanover, Salt Lake City, all of Utah

[73] Assignee: OEC Medical Systems, Inc., Salt Lake City, Utah

[21] Appl. No.: 806,417

[22] Filed: Feb. 26, 1997

Related U.S. Application Data

[60] Continuation of Ser. No. 425,881, Apr. 21, 1995, abandoned, which is a division of Ser. No. 209,961, Mar. 14, 1994, Pat. No. 5,426,683.

[51] Int. Cl.[6] .................................................. H05G 1/02
[52] U.S. Cl. .................... 29/897.35; 378/197; 72/256; 72/260
[58] Field of Search ........................ 29/897.31, 897.35, 29/897.3, 417, 527.7; 492/1; 378/193, 196, 197, 198; 72/256, 260, 215, 226, 205, 30.2, 369, 366.2; 264/177.17, 177.19, 281, 285

[56] References Cited

U.S. PATENT DOCUMENTS

| | | | |
|---|---|---|---|
| 3,742,748 | 7/1973 | Ehm | 72/369 |
| 4,204,309 | 5/1980 | Lefrancois | 72/256 |
| 4,432,123 | 2/1984 | Minning et al. | 72/369 |
| 4,977,771 | 12/1990 | Kimura | 72/215 |
| 5,104,026 | 4/1992 | Sturrus et al. | 72/369 |

*Primary Examiner*—Marc W. Butler
*Attorney, Agent, or Firm*—Thorpe, North & Western, LLP

[57] ABSTRACT

A one-piece C-arm for use with X-ray diagnostic equipment included in cross-section two generally vertical sidewalls extending generally parallel to one another, an inner support wall connecting the sidewalls, and an outer support wall spaced-apart from the inner support wall and connecting the sidewalls. A pair of flanges extend outwardly from respective sidewalls, and toward one another to form at least one channel along an outer portion of the C-arm frame for receiving wheels or bearings to allow moveable mounting of the C-arm on diagnostic equipment.

10 Claims, 4 Drawing Sheets

ONE PIECE C-ARM FOR X-RAY DIAGNOSTIC EQUIPMENT

This application is a continuation of application Ser. No. 08,425,881 abandoned Jul. 9, 1997, filed on Apr. 21, 1995 which was a divisional of application Ser. No. 08/209,961 filed Mar. 14, 1994 now U.S. Pat. No. 5,426,683.

BACKGROUND OF THE INVENTION

The present invention relates to a one-piece C-arm for X-ray diagnostic equipment and a method for making the same, and specifically to a seamless C-arm which is formed in a continuous curved piece to obviate the need for attaching two or more pieces together.

The use of "C-arms" for X-ray and other diagnostic equipment in surgical and other diagnostic procedures is well known in the medical arts. The mounting is referred to a C-arm due to the C-shape of the support frame which holds the diagnostic equipment in place. In use, an X-ray collimator or some other diagnostic device is mounted at one end of the frame. An image receptor is located on the other end so that the collimator and receptor are exactly opposite of each other.

There are two primary advantages to the C-shape of the support frame. First, the C-shape allows the diagnostic equipment to travel the length of the patient without interfering with the availability of the patient's body to medical personnel standing on the opposite side of the patient from the diagnostic equipment. Thus, a surgeon can operate on a patient while the C-arm travels up and down the body, ensuring that devices, such as angioplasty balloons, etc., are properly positioned during a procedure. A second advantage of the C-arm is that the arm can be rotated so that the collimator and the receptor are either nearly in the same vertical plane, nearly in the same horizontal plane, or somewhere in between. This rotation allows the radiologist or technician to take X-rays of the patient's body at an optimal angle for the anatomical structure being imaged. When a given patient is finished, the C-arm can be rotated to it original position, ready for the next patient.

One drawback of currently used C-arms is that they are usually formed of several pieces attached together in order to form tracks or channels which receive bearings or wheels to thereby allow the C-arms to rotate in the above described manner. For example, in U.S. Pat. No. 4,955,046, (Siczek et al.) there is shown a C-arm, the frame of which is formed in two pieces. The inner portion of the C-arm is formed in the shape of a flattened arch and attached, through an adhesive or some other manner, to an outer portion. Such a two piece C-arm frame is time consuming to fabricate and join and does not have the strength of a frame formed from a single, integral piece of material.

Another disadvantage of the C-arms of the prior art is that the C-arm is exposed to environmental contaminants. This comes about, for example, when C-arms are used in connection with surgical procedures, and the C-arm contacts bodily fluids, such as blood, or tissue being removed from a patient's body. With the current concern over tissue and fluid borne communicable diseases, it is desirable to keep the support arm free from contact with such contaminants.

In addition to contaminants from patients, the C-arm often encounters bacteria if used outside of the operating room. Such bacteria can be a serious threat to those undergoing surgery. Due to the size of the support arm, it is expensive and time consuming to thoroughly disinfect before each procedure.

Thus, a single piece C-arm formed to the desired shape would be desirable. Additionally, a C-arm which provides a support for a surgical drape/curtain or shield would also be advantageous to prevent contamination of the C-arm.

SUMMARY OF THE INVENTION

It is an object of the invention to provide an improved C-arm for use in diagnostic and surgical procedures.

It is another object of the invention to provide a C-arm support frame which is formed from a single piece of material.

It is an additional object of the present invention to provide an economical method for forming a C-arm support frame from a single piece of material.

It is yet another object of the invention to provide a structure for preventing bacteria and other contaminants from being passed between the patient and the C-arm.

The above and other objects of the invention are achieved by a C-arm frame having C-shaped unibody construction with a cross-section which includes two generally vertical sidewalls extending generally parallel to one another, an inner support wall connecting the sidewalls, and an outer support wall spaced apart from the inner support wall and connecting the sidewalls.

In accordance with one aspect of the invention, a pair of flanges extend upwardly from the outer support wall and then inwardly to form at least one channel along an outer portion of the C-arm frame, in which wheels or bearings may be mounted to enable the C-arm to rotate.

In accordance with another aspect of the invention, grooves are formed on the exterior of the vertical sidewalls, for receiving clips which, in turn, hold a surgical drape for preventing contamination of the C-arm.

DETAILED DESCRIPTION

Figure 1:
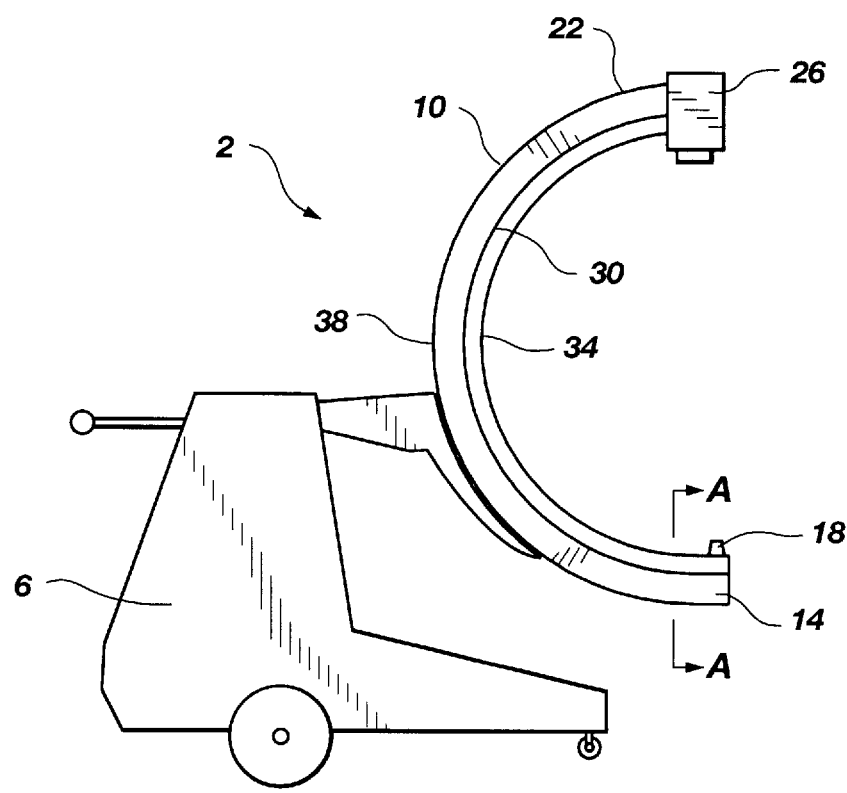
FIG. 1 shows a C-arm X-ray diagnostic machine made in accordance with a preferred embodiment of the invention.

Referring to FIG. 1, there is shown a side view of C-arm X-ray diagnostic equipment, generally indicated at 2, made in accordance with the present invention. The equipment 2 has a wheeled base 6 and a C-shaped support frame 10 connected to the base 6. Attached to a lower end 14 of the support frame 10 is an X-ray collimator 18. Positioned on the upper end 22 of the support frame 10 is an image receptor 26 for holding X-ray film and the like. The collimator 18 and the image receptor 26 are positioned so as to be opposite each other.

Positioned along the walls of the support frame 10 is a groove 30 which ideally extends from the upper end 22 to the lower end 14 of the support frame 10. The advantages of the groove 30 will be explained in detail with respect to FIGS. 2 & 3. The C-shaped support frame 10 has an inner circumference 34, which faces the X-ray diagnostic equipment 18 and 26, and an outer circumference 38 positioned opposite the inner circumference, the lower section of which faces the base 6.

Figure 2:
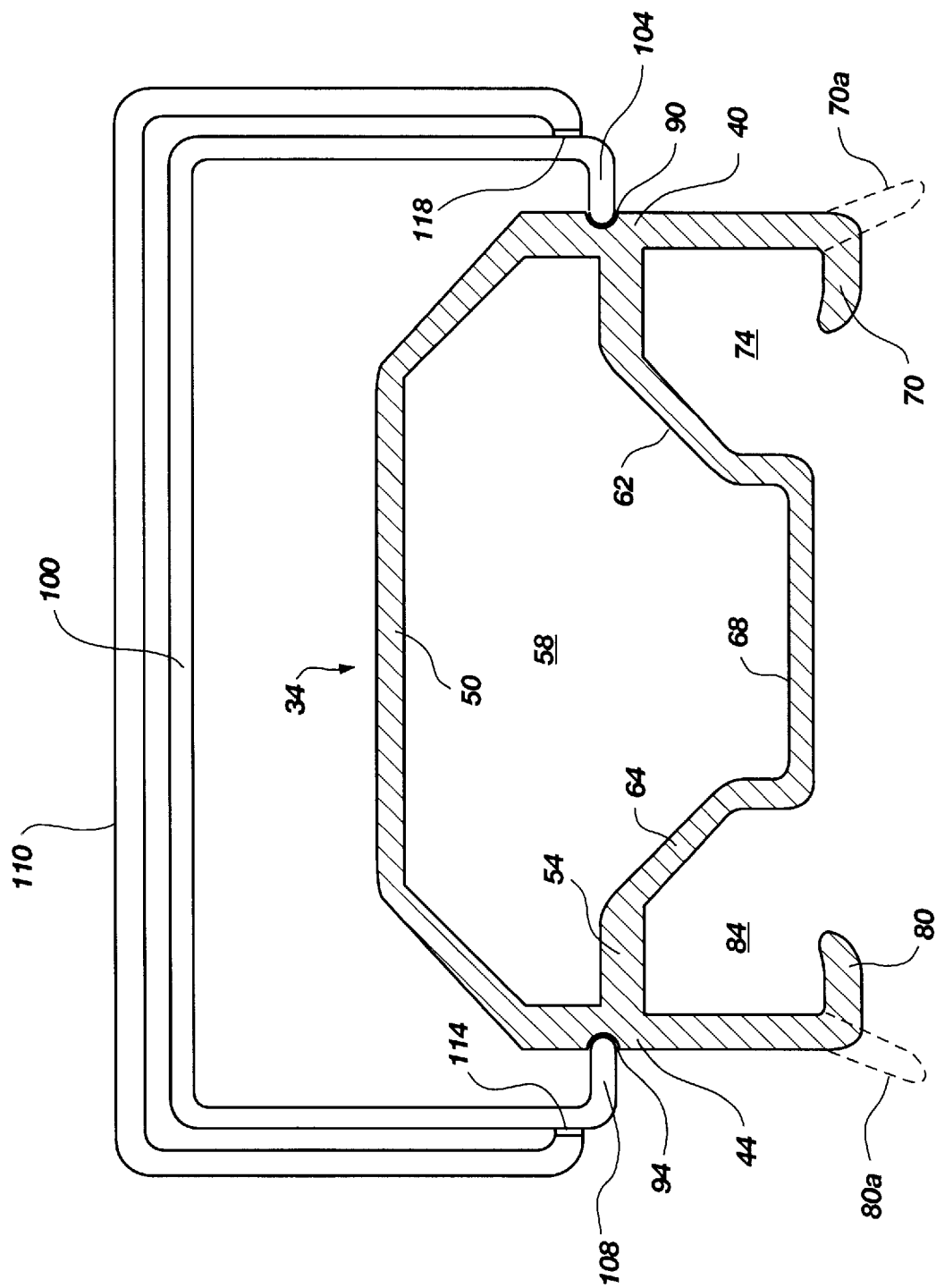
FIG. 2 shows a cross-sectional view of the C-arm frame taken along the lines A—A of FIG. 1, along with a surgical drape which is attached to the frame by a clip.

Referring now to FIG. 2, there is shown a cross-sectional view of the support frame 10 taken along the plane A—A shown in FIG. 1. Due to the location of the cross-sectional view, the inner circumference 34 is positioned at the top of the figure and the outer circumference 38 is positioned at the bottom of the figure. If the cross-section had been taken from the upper portion 22 (FIG. 1) of the support frame 10, the inner circumference 34 would be at the bottom and the outer circumference 38 would be at the top.

The cross-sectional view of FIG. 2 shows a pair of generally vertical sidewalls 40 and 44 which are separated by a pair of generally horizontal support walls 50 and 54. Unlike the sidewalls 40 and 44 which remain vertical for the length of the support frame 10, the support walls 50 and 54 curve in a C-shape such that the support walls are generally horizontal at the lower portion 14 and upper portion 22 of the support arm, but are generally vertical midway between the lower and upper portions.

A first, inner support wall 50 forms the inner circumference 34 of the C-shaped support frame 10. As shown in FIG. 2, the first support wall 50 is generally horizontal in the middle, and sloped on each end at about a forty-five degree angle to meet the vertical sidewalls 40 and 44. Those skilled in the art will recognize that there are many shapes which could be applied to the first support wall 50 to give structural support to the sidewalls 40 and 44, and thus the support frame 10. For example, the support wall 50 could be semi-circular, or arched. However, the configuration shown in FIG. 2 shows the present preferred embodiments for reasons which will be explained when discussing the method of making the support frame 10.

The second support wall 54 is positioned toward the outer circumference 38 of the support frame 10. The first and second support walls 50 and 54, together with the sidewalls 40 and 44, form a chamber 58 which extends the length of the support frame 10. In the preferred embodiment, the second support wall 54 extends horizontally from each sidewall, 40 and 44, and then has two angled sections 62 and 64 which extend outward (downward) at an angle to meet a generally horizontal section 68 positioned between the two.

A flange 70 extends from the sidewall 40 toward the horizontal section 68, so that the sidewall, the angled section 62 and the flange 70 form a channel 74 adjacent to the outer side 38 of the support frame 10. A flange 80 extends from the sidewall 44 toward the horizontal section 68, so that the angled section 64, the sidewall 44 and the flange 80 form a channel 84 adjacent to the outer circumference 38 of the support frame 10.

The cross-sectional view shown in FIG. 2 is that of the support frame 10 after it has been rolled into the C-shape shown in FIG. 1. When the support frame 10 is extruded, the flanges 70 and 80 area actually angled slightly outward—typically between about five and ten degrees from the sidewalls 40 and 44. This is represented by the dotted lines 70A and 80A adjacent each flange. As the extruded beam is rolled (see FIG. 4), the flanges 70 and 80 move into a position generally perpendicular to sidewalls 40 and 44, as shown in FIG. 2.

The channels 74 and 84 enable bearings or wheels to be positioned therein. When the wheels or bearings turn, the support frame 10 is rotated, thereby positioning the X-ray diagnostic equipment 18 and 26 at a desired angle. While the second support wall 54 could be straight (horizontal in FIG. 2), thereby forming only a single channel, the dual channel arrangement formed by the second support wall 54 provides additional strength and stability. Additionally, the channels 74 and 84 formed thereby allow more control over lateral movement of the wheels or bearings.

An important aspect of the support frame 10 as shown in FIG. 2 is that the frame is formed from a single piece. Prior art approaches had the first support wall and second support wall formed as two separate pieces which were then joined with adhesive, or by welding the two together. A two piece frame, however, is usually inferior structurally to one formed of a single piece of material.

Another aspect of the present invention that is shown in FIG. 2 is a pair of grooves 90 and 94 (equivalent to groove 30 in FIG. 1) formed in the sidewalls 40 and 44 respectively. The grooves 90 and 94 extend the length of the support frame 10 and enable a surgical drape to be placed about the inner circumference 34 of the support frame 10 to prevent contaminants from passing between the support frame 10 and a patient undergoing surgery.

Also shown in FIG. 2 is a clip 100 and a surgical drape 110 which is held to the frame 10 by the clip. The clip 100 is made of a resilient material, such as plastic, and has flanges 104 and 108 which nest in the grooves 90 and 94 to thereby hold the clip about the inner circumference 34 of the support frame 10. The surgical drape 110 is attached at each end to the clip 100 by fasteners 114 and 118. The fasteners 114 and 118, can be made of adhesive, formed as snaps, or comprise other fasteners known to those skilled in the art either currently or in the future.

The surgical drape 110 is held to the support frame 10 by placing one of the flanges 104 or 108 of the clip 100 into the respective groove 90 or 94 and deforming the clip slightly until the other flange is adjacent the other groove. Releasing the other flange causes both flanges to nest in the other groove, thereby holding the clip in place. The resilient nature of the clip 100 keeps the flanges 104 and 108 nested in the grooves 90 and 94 until an external force pulls the flanges from the grooves.

Figure 3:
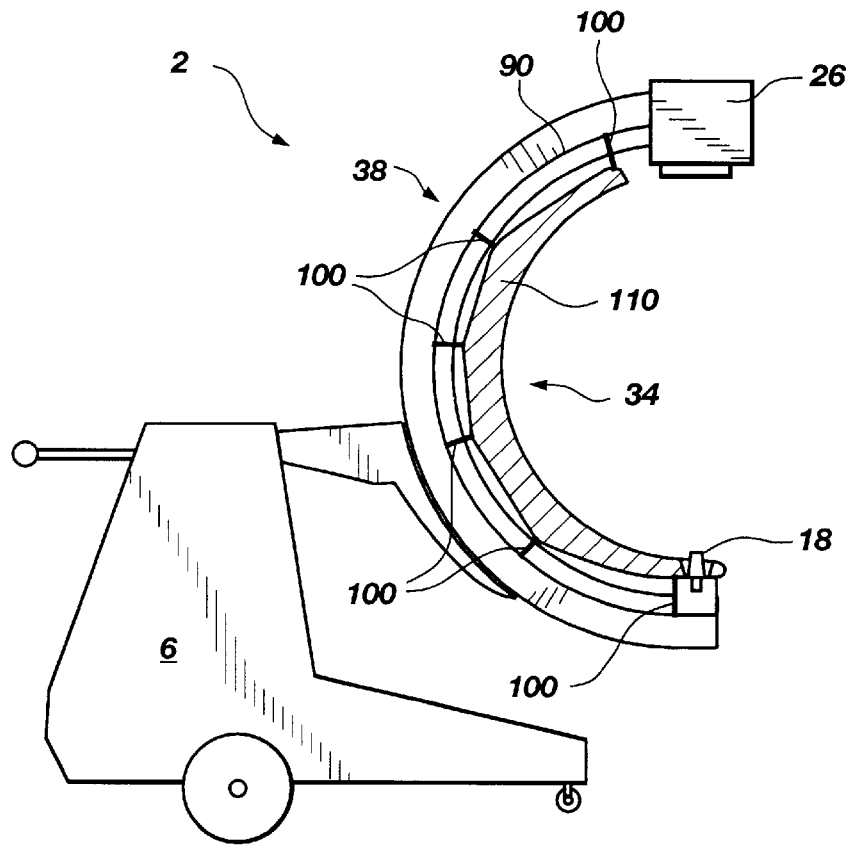
FIG. 3 shows a side view of a C-arm X-ray diagnostic machine having a surgical drape attached about the inner portion of the C-arm.

Referring now to FIG. 3, there is shown a side view of a C-arm similar to that shown in FIG. 1, but having a surgical drape 110 attached by a plurality of clips 100. The clips are anchored in the grooves, of which only groove 90 is shown. The purpose of the surgical drape 110 is to keep a sterile environment around the support frame 10. This can be difficult as C-arms are often used during surgical procedures. Tissue may fall on the C-arm and body fluids may occasionally spray, contaminating an uncovered support frame 10. By having a surgical drape 110 attached about the inner circumference 34 of the support frame 10, the risk of passing contaminants from the support frame to the patient or from the patient to the support frame are greatly reduced. Once a surgical procedure is over, the surgical drape 110 can be quickly and easily removed by disconnecting the clips 100. A new surgical drape can then be attached by another set of clips 100, or by reusing the original set with a new surgical drape/curtain 110.

In order to manufacture a unibody support frame 10 as has been described above, a material, such as metal or plastic, is extruded from a mold so that it has the desired cross-section. While the cross-section shown in FIG. 2 is a preferred embodiment, numerous other designs will be apparent to those skilled in the art.

Figure 4:
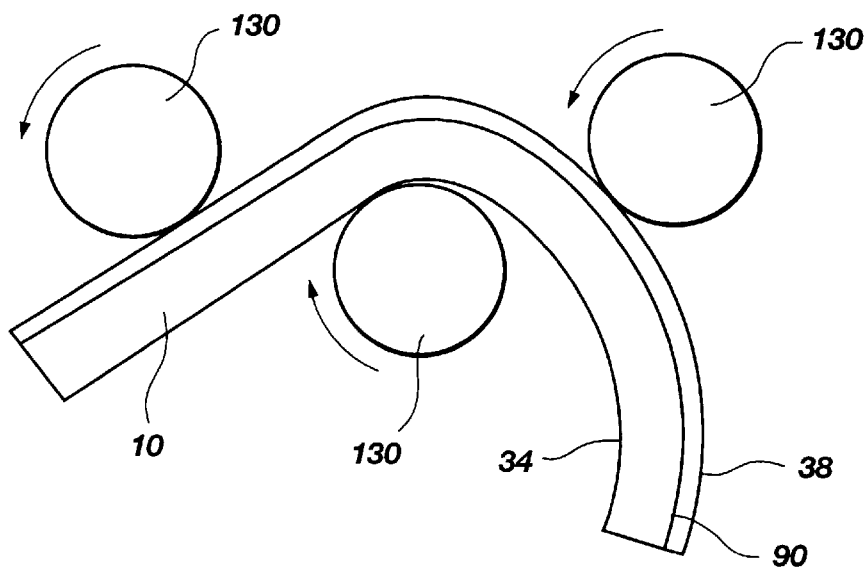
FIG. 4 shows a fragmented, side view of a piece of extruded material being formed/rolled into a C-shaped support frame for holding X-ray diagnostic equipment.

Referring to FIG. 4, there is shown a side view of an extruded metal frame 10 being passed through rollers 130 to give the frame the desired C shape. The originally straight frame 10 must be passed through rollers 130 with sufficient curvature so that the extruded material will not "spring" or relax back toward a straight element, but no so significant a curvature that the extruded material kinks, thereby weakening the support frame. The exact curvature of the rollers will depend in large part on design characteristics such as the desired size of the C-arm, the cross-sectional dimensions of the frame and the material from which the frame is made. As was alluded to earlier, the flat inner circumference 34 (FIG. 2) of the first support wall 50 is easier to curve without kinking than is a curved wall.

When using metal, the current preferred embodiment, the frame 10 is rolled at room temperature and a T4 temper. Usually, the frame 10 will be filled with sand or some other incompressible material to prevent the frame 10 from collapsing or kinking during the rolling process. After it has been rolled, the C-shaped frame 10 is heat treated to a T6 temper to provide additional strength. The C-shaped frame 10 can then be attached to X-ray diagnostic or other equipment.

Figure 5A:
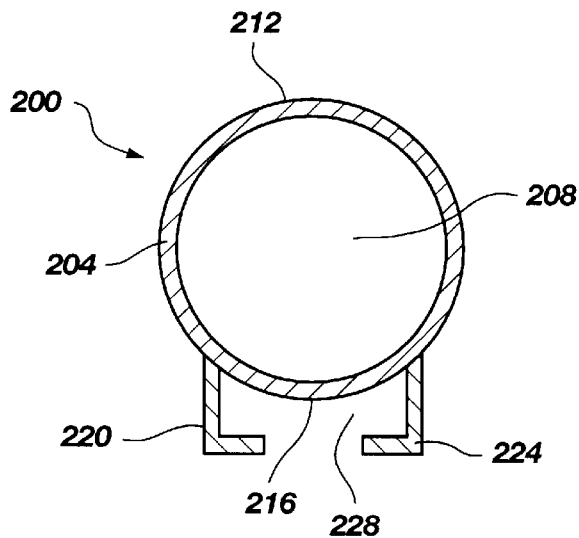
FIGS. 5A–C shows cross-sectional views similar to that of FIG. 2 for three alternate embodiments of the present invention.
Figure 5B:
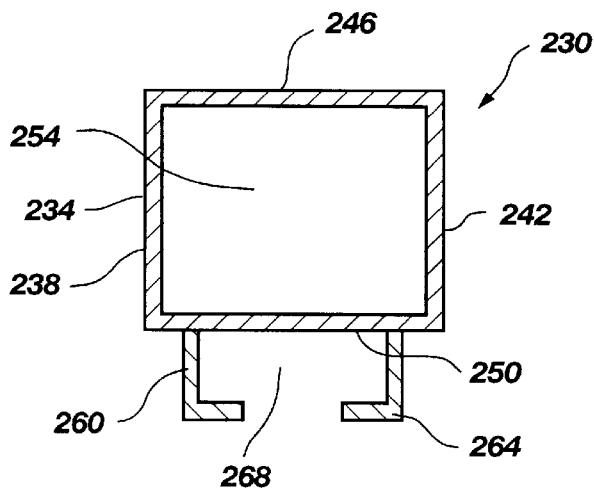
Figure 5C:
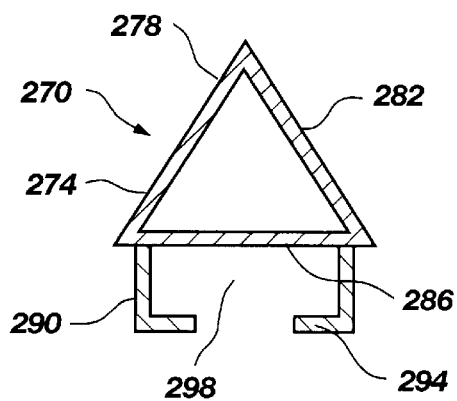

Referring now to FIGS. 5A–C, there are shown three alternate embodiments of the present invention. Each embodiment includes an elongate hollow piece of material. For ease of reference, the elongate hollow piece of material shall be referred to as a tube regardless of the cross-section shape of the material. In FIG. 5A there is shown a cross-section of a C-arm which a frame 200 including a tube 204 which is generally round and encloses a hollow 208. When bent in a C shape, the upper portion 212 of the tube 204 (which is analogous in function to the inner support wall in FIG. 2) will form the inner circumference of the C-arm frame. Accordingly, the lower portion 216 of the tube 204 (which is analogous to the outer support wall in FIG. 2) is positioned adjacent the outer circumference of the C-arm.

A pair of flanges 220 and 224 extend away from the tube 204, and then turn toward each other as to define a channel 228 between the flanges 220 and 224, and adjacent to the lower portion 216. When bearings (not shown) are placed in the channel 224, the frame 200 can be rotated as described above.

Referring now to FIG. 5B, there is shown a cross-sectional view of a frame 230 which has a tube 234 which is generally rectangular and encloses a hollow 238. The tube includes sidewalls 238 and 242 which are connected by spaced apart support walls 246 and 250. The sidewalls 238 and 242 and the support walls 246 and 250 enclose a hollow 254.

In the C-arm, the support wall 246 defines an inner circumference of the frame 230. The outer circumference of the frame 230 is formed by a pair of flanges 260 and 264 which extend from the outer support wall 250 and then turn toward each other to form a channel 268 between the flanges and adjacent the outer support wall.

Referring now to FIG. 5C, there is shown a frame 270 which includes a triangular tube 274 formed by two sidewalls 278 and 282 which are attached at one end and spaced apart by a support wall 286 at the other end. Two flanges 290 and 294 extend outward from the tube 274 and then turn towards each other to define a channel 298. In the C-arm, to point at which the sidewalls 278 and 282 join forms the inner circumference of the frame 270, while the flanges 290 and 294 define the outer circumference. Bearings (not shown) are positioned in the channel 298 to allow rotation of the frame 270 in the manner describe above.

With each of these embodiments, the frames 200, 230 and 270, respectively, are preferably formed of metal in the manner described with respect to the preferred embodiment. However, other materials such as plastic may also be used.

In the manner described above, an improved one-piece C-arm frame for X-ray diagnostic equipment is disclosed. It will be understood that other variations and modifications of the C-arm frame 10 will be apparent to those skilled in the art without departing from the scope of the invention. The C-arm frame described is not meant to be a delineation of the scope of the invention, but merely an example of a present preferred embodiment.

What is claimed is:

1. A method for forming a single piece C-arm for use with X-ray diagnostic equipment, the method including the steps of:

(a) extruding a material to form an elongate single piece beam sized with a cross-section including two generally vertical sidewalls connected by spaced-apart support walls configured so as to form a chamber between the two generally vertical sidewalls and spaced-apart support walls, and (b) successively passing the single piece beam through a plurality of rollers to curve the single piece beam and forming a generally C-shaped frame defining a C-shaped chamber between the two generally vertical sidewalls and the spaced apart support walls with opposing ends configured for attachment of X-ray diagnostic equipment.

2. The method of claim 1 wherein step (a) further comprises forming two flanges extending from respective sidewalls and generally toward each other to form at least one channel along a section of the single piece beam.

3. The method of claim 1 wherein the material extruded in step (a) is selected from the group consisting of aluminum and plastic.

4. The method of claim 1 wherein step (b) further comprises passing the single piece beam through the rollers while the single piece beam is hot.

5. The method of claim 4 further comprising clamping the single piece beam in a C-shape and allowing the single piece beam to cool.

6. A method for forming a single piece C-arm for use with X-ray diagnostic equipment, the method including the steps of:

(a) extruding a material to form an elongate single piece beam having an enclosed chamber and a pair of outwardly extending flanges configured to define a channel for receiving bearings, and (b) successively passing the single piece beam through a plurality of rollers to curve the single piece beam and forming a generally C-shaped frame defining a C-shaped chamber and C-shaped channel between the two generally vertical sidewalls and the spaced apart support walls with opposing ends configured for attachment of X-ray diagnostic equipment.

7. The method of claim 6 wherein step (a) further comprises forming the pair of outwardly extending flanges extending generally toward each other to form the channel for receiving bearings.

8. The method of claim 6 wherein the material extruded in step (a) is selected from the group consisting of aluminum and plastic.

9. The method of claim 6 wherein step (b) further comprises passing the single piece beam through the rollers while the single piece beam is hot.

10. The method of claim 9 further comprising clamping the single piece beam in a C-shape and allowing the single piece beam to cool.

* * * * *